United States Patent [19]

Nakano

[11] Patent Number: 4,495,632
[45] Date of Patent: Jan. 22, 1985

[54] RADIOGRAPHIC APPARATUS FOR PHOTOGRAPHING ENTIRE JAWS

[75] Inventor: Kozo Nakano, Kyoto, Japan

[73] Assignee: Kabushiki Kaisha Morita Seisakusho, Kyoto, Japan

[21] Appl. No.: 575,317

[22] Filed: Jan. 30, 1984

Related U.S. Application Data

[63] Continuation of Ser. No. 277,721, Jun. 26, 1981, abandoned.

[30] Foreign Application Priority Data

Jun. 27, 1980 [JP] Japan ................................ 55-88058

[51] Int. Cl.³ ............................................. G03B 41/16
[52] U.S. Cl. ......................................... 378/40; 378/38
[58] Field of Search ............................. 378/38, 39, 40

[56] References Cited

U.S. PATENT DOCUMENTS 4,264,820  4/1981  Hotta ..................................... 378/40

Primary Examiner—Craig E. Church
Attorney, Agent, or Firm—Koda and Androlia

[57] ABSTRACT

This disclosure relates to a dental radiographic apparatus for photographing the entire jaws designed to control the rotation of a rotary arm such that the film surface of a film holder mounted at one end of the rotary arm may rotate and move substantially at equal speed substantially equidistantly along the dental arch and that the X-ray beams irradiated upon the film surface from an X-ray generator mounted at the other end of the arm may fall on the dental arch at any point thereof at right angles with the arch. The apparatus makes it possible to obtain a very clear tomographic picture of a curved plane of the entire jaws, the picture being free of a double image of the teeth, partial change in enlargement ratio of the image obtained, and partial difference in the shade of the image obtained.

3 Claims, 5 Drawing Figures

RADIOGRAPHIC APPARATUS FOR PHOTOGRAPHING ENTIRE JAWS

This is a continuation of application Ser. No. 277,721, filed June 26, 1981 now abandoned.

BACKGROUND OF THE INVENTION

1. Field of the Invention

This invention relates to a dental radiographic apparatus for obtaining an X-ray photographic picutre of a curved plane section of the entire jaws of a patient.

2. Prior Art

The dental radiographic apparatus for photographing the entire jaws comprises an arm rotatably mounted on a support, an X-ray generator mounted at one end of the arm, and a film holder mounted at the other end of the arm in an opposed relation with the X-ray generator, and is designed to take a tomographic picture of the curved plane of the entire jaws of a patient by irradiating X-ray beams from the generator upon the film surface in the film holder while rotating the generator and the film holder around the head of the patient by rotating the arm. Since the tomographing of the curved plane of the entire jaws conducted by the apparatus of the type described makes it possible to provide a panoramic picture of the entire jaws to enable overall inspection of the entire jaws at a glance, the apparatus has become indispensable for the overall examination not only of the individual tooth but also of the entire jaws.

However, although it is of course necessary that the radiographic image of the entire jaws be clear and vivid, the apparatuses heretofore in use have many problems to be solved. One of the conventional apparatuses is designed such that the rotation center of the arm is stepwise changed during the rotation to thereby make the film holder rotate, describing an elliptical locus composed of three circles. However, since such apparatus made it necessary to change the rotation center of the arm three times while photographing the apparatus involved a problem to make a photographic image unclear before and after such changes. In an attempt to solve the problem of the kind described, the present applicant earlier provied a radiographic apparatus (Japanese patent application No. 53165/1972) constructed in such a manner that a film holder is smoothly rotated tracing an elliptical locus by forming a cross groove on a support, providing the arm with two projections, and continuously changing the rotation center of the arm while sliding the two projections in the cross groove in accordance with the rotation of the arm. The apparatus had an advantage in that the same can satisfactorily solve the problem of the kind described, while on the other hand, the apparatus had a disadvantage in that the teeth contiguous to each other are photographed in a double image on the portion where X-ray beams from the X-ray generator fell slantly upon the dental arch and had another disadvantage in that the image of each tooth is different in enlargement ratio.

In view of the above disadvantages, the applicant later filed a patent application for a radiographic apparatus (Japanese patent application No. 97303/1974) constructed in such a manner that the support is provided with an arcuate groove and a linear groove passing through the center of the arcuate groove and the arm is provided with the aforestated two projections and a film holder can be rotated smoothly describing an elliptical locus and X-ray beams may fall on any point of the dental arch at right angles with the dental arch. Since the apparatus made it possible for the X-ray beams to fall on the dental arch intersecting the dental arch at right angles, the apparatus was enabled to remove the disadvantage of a double image of the teeth contiguous to each other but nevertheless there still remained such drawback that an arm driving roller slipped sideways in its rotation with respect to the support to render the movement of the arm instable.

SUMMARY OF THE INVENTION

An object of the invention is to eliminate all the aforestated inherent disadvantages in the prior art apparatuses, namely, such disadvantages as partial blur of a photographic picture of a tooth, a double image of a tooth, non-uniformity in enlargement ration, and instability of arm movement.

Another object of the invention is to prevent partial difference in the shade produced in the image photographed.

The objects of the invention can be achieved by providing a support with a swing member rotatably in such a manner that the member may make arcuate movement without rotating on its own axis, by forming a projection on one of the opposed surfaces of the support and arm and forming a curved groove on the other of the surfaces, by controlling the rotation of the arm both by guide of the projection by the guide groove and by the arcuate movement of the swing member in such a manner that the film surface of the holder may be kept substantially at a certain distance and may be moved at equal speed along the dental arch and the X-ray beams irradiated from the X-ray generator upon the surface may fall on any point of the dental arch substantially at right angles therewith.

A detailed description of a preferred embodiment of the invention will now be given by way of example only with reference to the accompanying drawings.

DETAILED DESCRIPTION OF THE INVENTION

Figure 4:
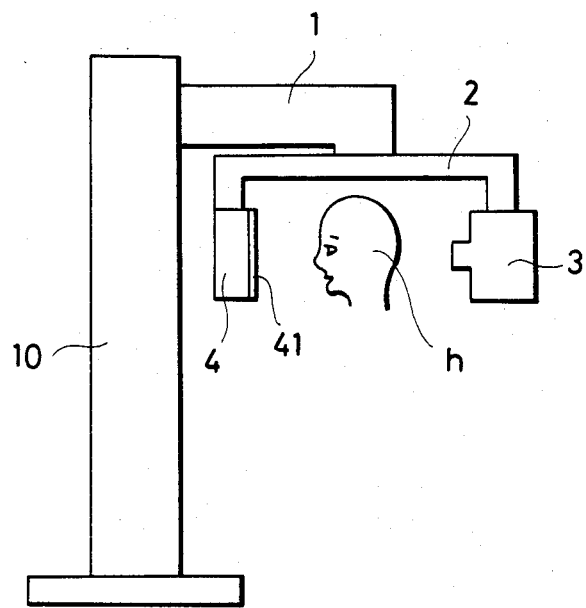
FIG. 4 is a side view typically showing the apparatus of the invention.
Figure 5:
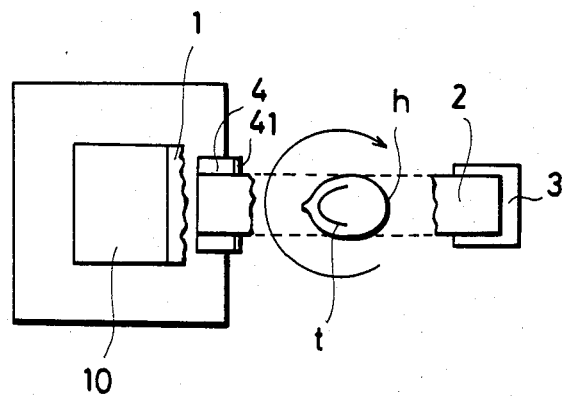
FIG. 5 is a plan view, broken in part, typically showing the apparatus of the invention.

The dental radiographic apparatus of the invention for photographing the entire jaws is the same in general structure and operating principle as the conventional apparatuses. Namely, the apparatus of the invention, as shown in FIGS. 4 and 5, includes at least an arm 2 rotatably mounted on a support 1 projecting from a stanchion 10, an X-ray generator 3 mounted at one end of the arm 2, and a film holder 4 mounted at the other end of the arm 2 in an opposed relation with respect to the X-ray generator 3, and is designed to obtain an X-ray photograph of a predetermined curved palne section of the entire jaws of a patient by irradiating the X-ray beams from the X-ray generator 3 upon the film surface 41 of the film holder 4 while rotating the X-ray generator 3 and the film holder 4 around the head h of a patient by rotating the arm 2.

The characteristic features of the invention lie in the mounting structure by which the arm 2 is made rotatable with respect to the support 1.

Figure 1:
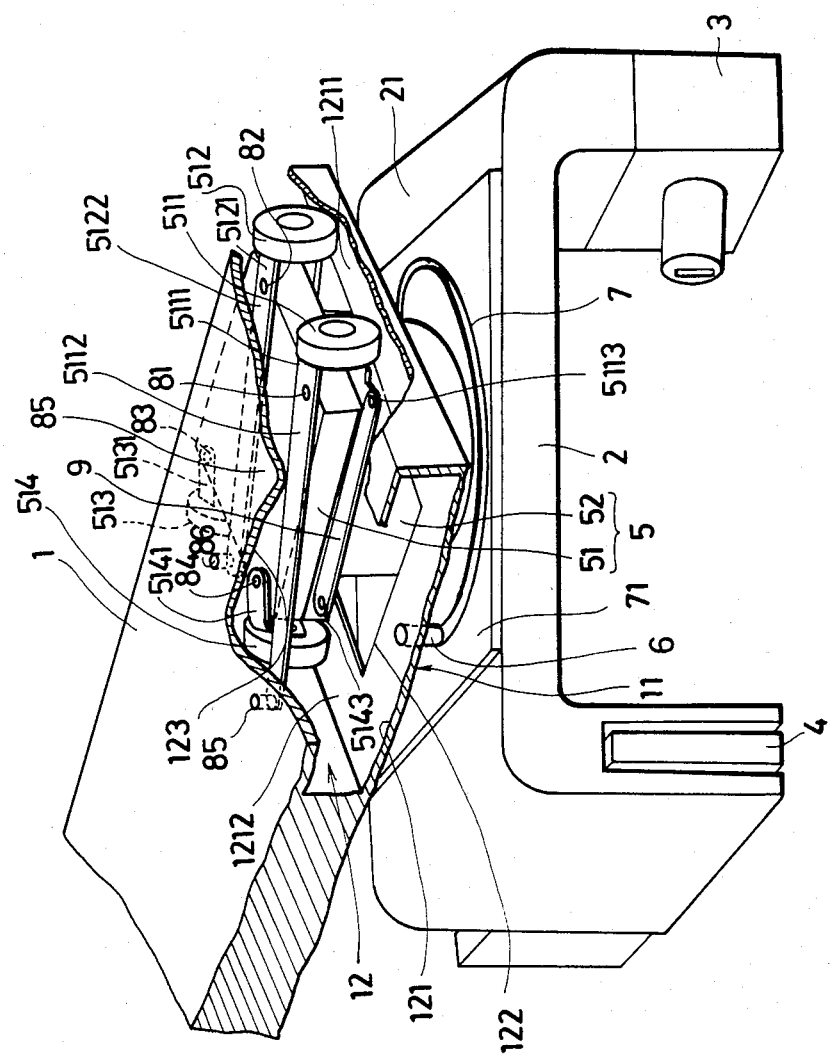
FIG. 1 is a perspective view, broken in part, of the essential part of the apparatus of the invention.
Figure 2:
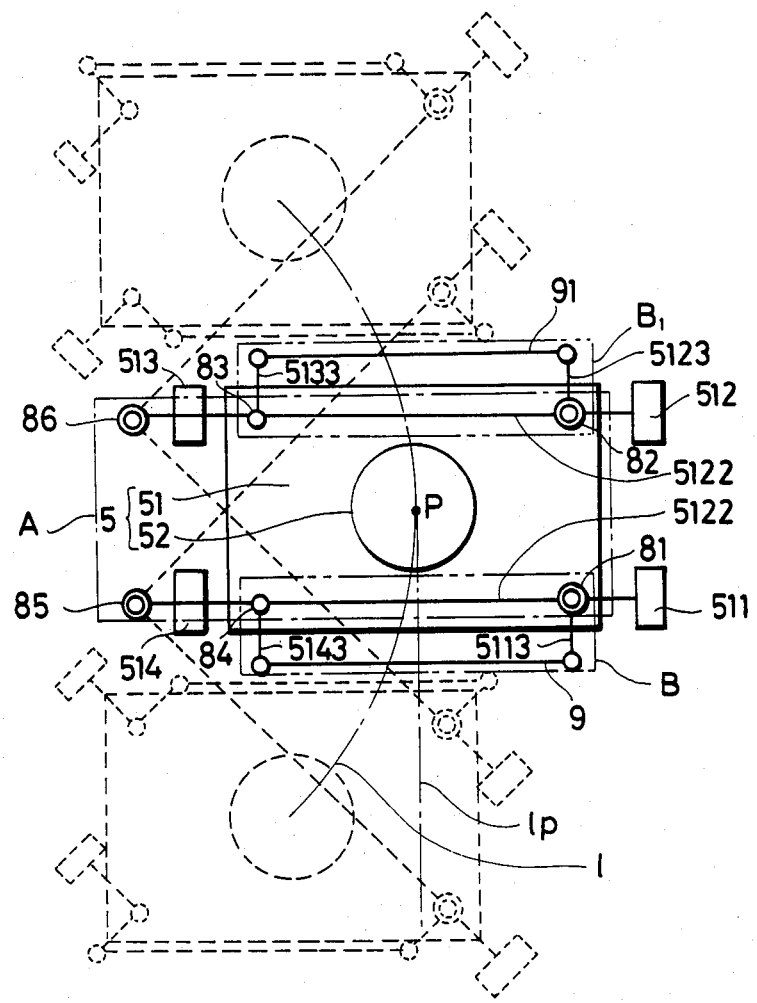
FIG. 2 is an explanatory diagram illustrating the operation of a swing member.

Referring to the structure of the invention in conjunction with FIGS. 1 and 2, the support 1 is formed at the end thereof with a hollow chamber 12, in which a swing member 5 is contained. The swing member 5 is made up of a square swing plate 51 formed thereunder integrally with a vertical shaft 52, the vertical shaft 52 projects downwardly through an opening 122 of the bottom wall 121 of the chamber 12 and has the arm 2 rotatably mounted at the lower end portion of the vertical shaft 52. The swing plate 51 of the swing member 5 is provied with roller 511, 512, 513 and 514 and these rollers bear the swing member 5 in such a manner that the rollers 511 and 512 roll along the open front edge portion 1211 of a bottom wall 121 of the chamber 12 and the rollers 513 and 514 roll along the open rear edge portion 1212 of the bottom wall 121. Fittings 5111, 5121, 5131 and 5141 for the rollers are U-shpaed in section and are pivotally mounted to the swing plate 51 to be permitted to rotate respectively by pins 81, 82, 83 and 84 in the state that the U-shaped fittings are gripping the front edge portion and the rear edge portion of the swing plate 51 from upper and lower sides. In those fittings, two fittings 5111 and 5121 connected pivotally to the front edge portion of the swing plate 51 have, respectively, extended upper portions to provide links 5112 and 5122. The base end portions of the links 5112 and 5122 are pivotally connected by pins 85 and 86 to the upper wall 123 of the hollow chamber 12 of the support 1 to permit links 5112 and 5122 to rotate with respect to the upper wall to construct a parallel linkage A (see FIG. 2) using the pins 81, 82, 85 and 86 as pivots. Furthermore, outwardly projecting segments are formed integrally with the lower segements of the U-shaped fittings 5111, 5121, 5131 and 5141 and a link 9 is spanned between a segment 5113 of the fitting 5111 and a segment 5143 of the fitting 5121 and a similar link 91 is also spanned between a segment 5123 of the fitting 5121 (see FIG. 2) and a segment 5133 of the fitting 5131 (see FIG. 2) so as to provide pivotal connection between the respective links and branch segments to be permitted to rotate therebetween to thereby construct two parallel linkages B and $B_1$ (see FIG. 2).

Accordingly, the swing member 5, as shown in FIG. 2, is enabled by the parallel linkage A to keep invariably certain directivity without rotation on its own axis and to move in such a manner that the center of the swing member 5 may describe an arcuate locus l. When the swing member 5 moves, all the four rollers 511, 512, 513 and 514 roll in the same direction by cooperation of three parallel linkages A, $B_1$, and B, namely, in the direction of tangent lp at any point P at which the swing member 5 on the arcuate locus l is positioned, with the result that the arcuate movement of the swing member 5 is smoothly effected.

On the underside 11 of the bottom wall 121 of the hollow chamber 12 of the support 1 is fixed a downwardly extending projection 6, and on the upside of the arm 2 is fixed a plate 71 having a curved guide groove 7 formed thereon into which the projection 6 is fitted. The guide groove 7, as shown in FIG. 3, is an approximate semicircular groove fromed in approximate spiral with respect to the center of rotation of the arm 2, namely, with respect to the axis of the vertical shaft 52 of the swing member 5 and is gradually different in distance from the axis to each point of the guide groove 7.

The curved configuration of the guide groove 7 is determined in the following manner. First, as shown in solid line in FIG. 3, the arm 2 is faced substantially normally to the support 1 so tht the X-ray generator 3 is placed opposite to the fixed projection 6 of the support 1 with the centerline C of the support 1 set therebetween and a film holder 4 may be positioned on the same side on which the projection 6 is placed. At this time, the swing member 5 having the arm 2 pivotally connected thereto is kept displaced to one end side of the arcuate locus l, namely, the side opposite the fixed projection 6 with centerline C set therebetween. Then, the arm 2 is rotated clockwise from this state through about 180°. The arm 2 is rotated to cause the swing member 5 to move continuously at unequal speed along the arcuate locus l so as to satisfy two conditions, namely, moving of the film surface 41 of the film holder 4 substantially at equal speed along an approximate semi-elliptical curve T positioned substantially at equal distance from the dental arch t and falling of X-ray beams b to be irradiated from the X-ray generator 3 on each point of the dental arch t at right angles with the dental arch. When the arm 2 is rotated in this manner, the fixed projection 6 travels on the upper surface of the arm 2 in an opposed relation with respect to the arm 2 to describe an approximate semicircular locus of movement. The curved configuration of the guide groove 7 is the configuration obtained by correctly bringing the movement of the arm 2 into the agreement with thus found locus of relative movement of the projection 6.

Figure 3:
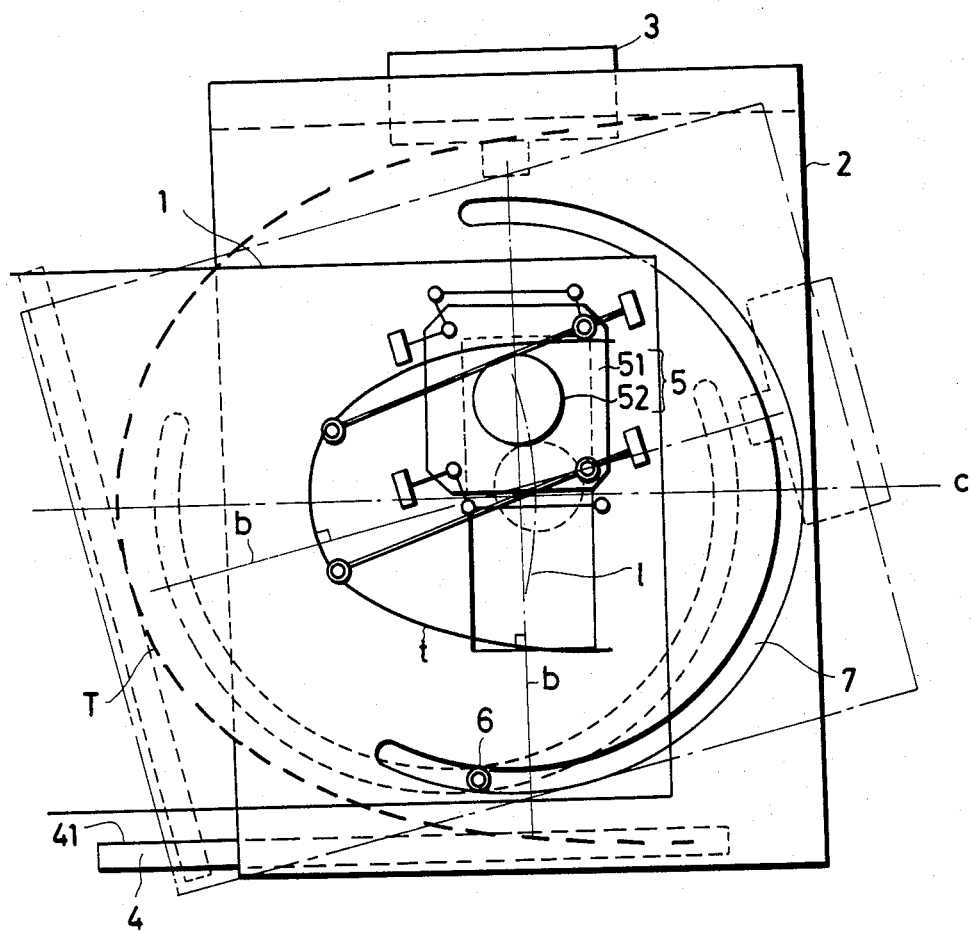
FIG. 3 is an explanatory diagram illustrating the operation of an arm.

Accordingly, when in the invention the arm 2 is clockwise rotated at equal speed by a driving means (not shown) from the solid line state in FIG. 3, the arm 2 moves continuously at unequal speed around the center of rotation along the arcuate locus l by the control of arcuate movement of the swing member 5 in cooperation with the guide of the projection 6 by the guide groove 7, and the film surface 41 rotates and moves on an approximate elliptical curve T substantially at equal speed and makes particularly rotational movement which makes it possible for the X-ray beams b to be incident on the dental arch t approximately at right angles with the arch t.

In the embodiment illustrated, the projection 6 is formed on the support 1 and the guide groove 7 is formed on the arm 2, but it should be understood that formation of the projection and groove may be reversed in position without any effect on operation. As apparent from this, all that is necessary is to form the projection 6 on either one of the opposing faces 11 and 21 of the support 1 and the arm 2 and to form the groove 7 on the other thereof. However, when the groove 7 is formed on the upper surface 21 of the arm 2, the arm must be wide enough to have the groove 7 formed thereon, while in contrast thereto, when the groove 7 is formed on the support 1 side, no such broad arm 2 is necessary, with the result that the load of the support 1 is reduced in proportion to the weight of the arm 2 for the advantage of the apparatus.

According to the aforestated structure of the invention, the film surface 41 of the film holder 4 rotates on an approximate elliptical curve T substantially equidistant from the dental arch t and X-rays beams b falls on the dental arch t at any point thereof substantially at right angles with the dental arch t, with the result that the photographic image is made constant in enlargement ratio to thereby assure prevention of double image photographing of the teeth. Moreover, the axis shaftline of the vertical shaft 52 of the swing member 5 which constitutes the center of rotation of the arm 2 makes arcuate movement at unequal speed but continuously, so that the apparatus can sufficiently eradicate the drawback of such blurred image before and after the change as has been made in the conventional apparatuses in which the center of rotation of arm uncontinuously undergoes three stages of change. Furthermore, since the swing member 5 is designed to make arcuate movement with no self-rotation but with its definite directivity kept by a parallel linkage A, rotation of the arm 2 at certain speed with respect to the swing member 5 makes it possible to rotate and move the film surface 41 of the film holder 4 substantially at equal speed along the approximate elliptical curve T, resulting in the constant maintenance of the amount of X-rays irradiated on the film surface 41 to thereby provide a clear image having no partial difference in shade. This effect cannot be obtained, because if, for example, the swing member 5 is constructed in such a manner that the axis of the vertical shaft 52 may make arcuate movement by making the swing member 5 rotatable at one end through pivotal connection, the swing member 5 itself rotates on its own axis at unequal speed and accordingly, even if the arm 2 is rotated at constant speed with respect to the member 5, the film surface 41 is not allowed to make rotational movement along the approximate elliptical curve T at equal speed.

I claim:

1. An X-ray photographic apparatus for taking a radiograph of the entire jaws comprising a first support, a second support mounted on said first support so as to permit arcuate movement of the second support without rotating about an axis which passes through the second support, an arm mounted rotatably on said second support and having an X-ray generator on its one end and a film holding means in opposed relation with the generator a means for rotating said arm, a means for arcuately moving said second support when said arm is rotated, a single projection provided on either one surface of opposed surfaces of said first support and said arm, and a single curved guide groove provided on the other surface for slidably guiding said projection fitted into the inside of the other surface through said guide groove, said guide groove being generally semi-circular and of such a shape such that movement of the single projection in the single guide groove and arcuate movement of said second support during rotation of said arm control the rotation of said arm, rotates the film surface in said film holding means along the dental arch at an approximately constant distance from the arch and at an approximately equal speed and causes the X-ray beams from said X-ray generator to irradiate onto the film surface at right angles to the plane of the dental arch at any point of the arch.

2. An apparatus according to claim 1, wherein said means for arcuately moving said second support when said arm is being rotated is constructed such that said arm is rotatably mounted on a lower end of said second support which is received in a hollow chamber formed in said first support projecting downwardly from an opening of the bottom wall of said hollow chamber and a pair of parallel links is rotatably provided on said first support by two pins provided on said first support.

3. An apparatus according to claim 1, wherein said second support has four rollers for supporting itself, all of said rollers being constructed so as to automatically change direction thereof corresponding to the direction of arcuate movement of said second support.

* * * * *